United States Patent [19]

Saleme

[11] Patent Number: 4,764,991
[45] Date of Patent: Aug. 23, 1988

[54] FEMALE URINAL FOR SUPINE USE

[76] Inventor: Lola M. Saleme, 177 Bigelow St., Brighton, Mass. 02135

[21] Appl. No.: 52,521

[22] Filed: May 21, 1987

[51] Int. Cl.$^4$ ............................................. A47K 11/12
[52] U.S. Cl. ....................................................... 4/144.1
[58] Field of Search ........................... 4/144.1–144.4; 128/760, 761, 767; 604/327–331, 347, 350, 354

[56] References Cited

U.S. PATENT DOCUMENTS

| | | | |
|---|---|---|---|
| 4,023,216 | 5/1977 | Li | 4/144.3 |
| 4,050,103 | 9/1977 | Nakao et al. | 4/144.3 |
| 4,106,490 | 8/1978 | Spilman et al. | 128/761 |
| 4,121,306 | 10/1978 | Bringman et al. | 4/144.2 |
| 4,202,058 | 5/1980 | Anderson | 4/144.3 |
| 4,233,978 | 11/1980 | Hickey | 4/144.3 X |
| 4,528,703 | 7/1985 | Kraus | 4/144.3 X |
| 4,531,245 | 7/1985 | Lowd et al. | 4/144.3 |
| 4,568,339 | 2/1986 | Steer | 4/144.3 X |

*Primary Examiner*—Charles E. Phillips
*Attorney, Agent, or Firm*—Henderson & Sturm

[57] ABSTRACT

A urinal for use by a female person in lying in a supine position. The urinal includes a container having a substantially circular open top defined by a top rim portion. The flexible container has a closed bottom portion and encircling side walls. A short arcuate portion on the rim of the flexible container is designed for contact with the appropriate body parts of such female person for causing urine flowing from such female person to flow into the container and not flow around or below such rim portion. A first conduit is attached to a bottom portion of the flexible container and is in fluid communication with the bottom portion of such container. A bottle is provided for collecting and storing urine which flows from the flexible container to the bottle, such bottle having an opening in the bottom thereof. A cap is provided for selectively opening or closing such opening in the bottle. A second conduit is attached in fluid communication with the top of the bottle and a flexible hose is attached in fluid communication with the first conduit on the container and the second conduit on the bottle for causing urine in the container to flow from the flexible container to the bottle when the bottle is disposed below the flexible container.

1 Claim, 1 Drawing Sheet

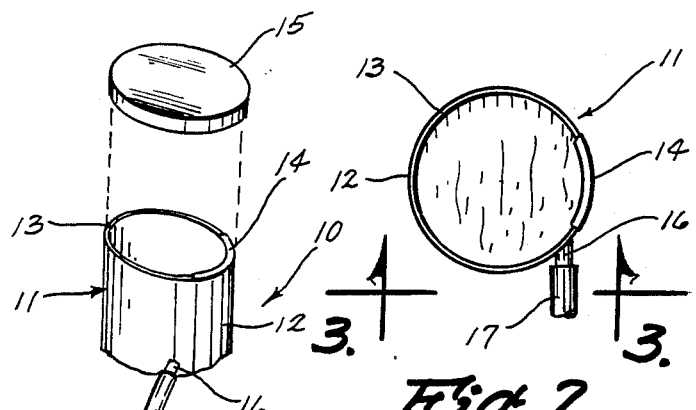
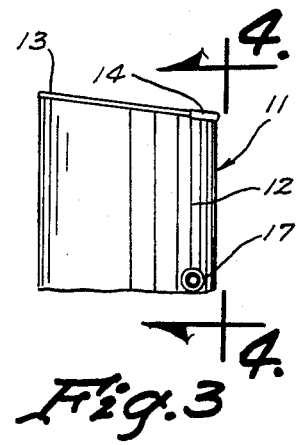
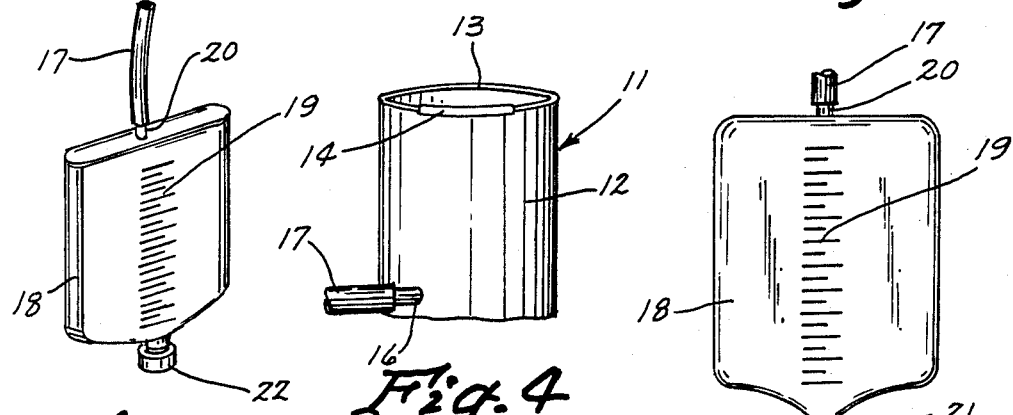
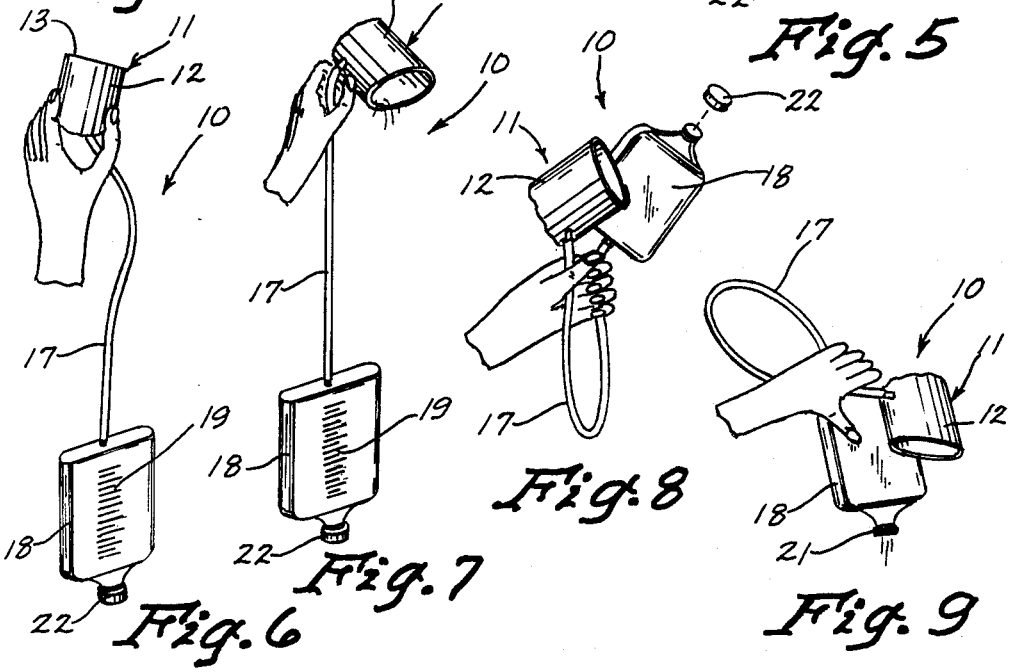
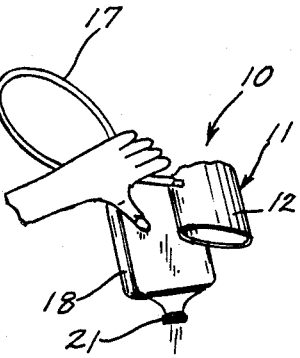

FEMALE URINAL FOR SUPINE USE

This invention is an improvement on the subject matter of my previously abandoned U.S. patent application Ser. No. 764,584 filed Aug. 12, 1985 and entitled "Female Urinal For Supine Use".

TECHNICAL FIELD

The present invention relates to equipment useful at a sick bed, and more particularly to improvements in female urinals intended for supine use.

BACKGROUND ART

Various female urinals have been devised for the purpose of being utilized by a female person lying in bed in the supine position. U.S. Pat. No. 4,202,058 to Anderson shows one proposed solution to the problem. In this patent a structure is shown to be strapped to such female person and sealed around the appropriate body parts in order to receive urine and guide it to a collection chamber. One of the problems with the prior art as exemplified by the above mentioned patent is that it that the prior art devices are uncomfortable and difficult to use. Furthermore, such prior art devices are difficult to empty.

Consequently, there is a need for an improved urinal for use by a female person in the supine position.

DISCLOSURE OF THE INVENTION

The present invention relates to a urinal for use by a female person in lying in a supine position. The urinal includes a flexible container having a substantially circular open top defined by a top rim portion. The container has a closed bottom portion and encircling side walls. A special sealant section comprising a short arcuate portion is formed on a segment of the rim of the flexible container and is specifically designed deformable lip for contact with the appropriate body parts of such female person for causing urine flowing from such female person to flow into the container and not flow around or below such rim portion. A first conduit is attached to a bottom portion of the flexible container and is in fluid communication with the bottom portion of such container. A bottle is provided for collecting and storing urine which flows from the flexible container to the bottle, such bottle having an opening in the bottom thereof. A cap is provided for selectively opening or closing such opening in the bottle. A second conduit is attached in fluid communication with the top of the bottle and a flexible hose is attached in fluid communication with the first conduit on the flexible container and the second conduit on the bottle for causing urine in the container to flow from the flexible container to the bottle when the bottle is disposed below the container.

An object of the present invention is to provide an improved urinal for use by a female person in the supine position whereby the female will be able to wipe herself prior to the urinal being taken away so that there will be no drips of urine deposited.

Another object of the invention is to provide an improved urinal of the aforementioned type which has a collecting bottle attached thereto and having an opening in the bottom thereof which can be opened to easily either store the urine or dispose of it.

Other objects, advantages, and novel features of the present invention will become apparent from the following detailed description of the invention when considered in conjunction with the accompanying drawings.

BRIEF DESCRIPTION OF THE DRAWINGS

FIG. 1 is a perspective view of a preferred embodiment of the present invention and showing it with the lid of the container removed;

FIG. 2 is a view of the top of the urinal constructed in accordance with the present invention;

FIG. 3 is a side elevational view of the urinal as viewed along line 3—3 of FIG. 2;

FIG. 4 is a side elevational view of the urinal as viewed along line 4—4 of FIG. 3;

FIG. 5 is a side elevational view of the bottle shown in FIG. 1;

FIG. 6 is a perspective view showing the urinal in use for collecting urine within a flexible container and having a bottle available to collect the urine which can flow from the flexible container into the bottle;

FIG. 7 shows how the flexible container can easily be emptied;

FIG. 8 shows how the cap can be removed from the bottle without the urine flowing out therefrom; and FIG. 9 shows how the urine can be removed from the bottle and emptied into a toilet or the like so that the urinal can be used again.

BEST MODE FOR CARRYING OUT THE INVENTION

Referring now to the drawings, wherein like reference numerals designate identical or corresponding parts throughout the several views, FIG. 1 shows a urinal (10) constructed in accordance with the present invention. The urinal (10) includes a generally flexible container (11) having side walls (12) and a top rim portion (13) surrounding an enlarged oversized generally circular opening.

As shown in FIG. 3, the container (11) is formed from a segment of a right circular cylinder having a closed bottom and a top rim portion (13) formed by a plane passing through the right circular cylinder at an angle other than perpendicular to the longitudinal axis of the cylinder thereby forming an uppermost and a lowermost segment on the top rim portion (13) of the container. In addition, the top rim portion includes a special sealant section (14). The special sealant comprises a short arcuate deformable lip portion (14') which is formed on a segment of the rim portion (13) of the generally flexible container (11) wherein the modules of elasticity of the material of the sealant section (14) is substantially greater than the modules of elasticity of the material from which the rest of the container (11) is constructed. An example of the preferred material chosen for use in the fabrication of the generally flexible container (11) and the special sealant section (14) would constitute plastic and latex materials, respectively. This will facilitate ease of use and comfort to the person using it. A cap (15) is provided for closing the top of the container (11), when such container is not in use.

The container (11) has a conduit (16) attached to a bottom portion thereof, for example as shown in FIGS. 1–4. This conduit (16) has a rubber or plastic hose (17) attached in a sealing fashion thereto and this hose (17) extends down into fluid communication with a plastic bottle (18) having indicia (19) thereon for determining how much urine is contained within the bottle (18). This bottle (18) has a conduit (20) attached thereto in fluid communication with the bottle (18) and the hose (17) is sealingly attached to the conduit (20). The bottle (18) has a threaded opening (21) on the bottom thereof for threadably receiving a cap (22) which can be utilized to open or close the bottom of the bottle (18).

When it is desired to utilize the urinal (10), the bottle (18) would be placed in a position lower than the patient, so that it could be extending over the edge of a bed or the like. The container is then placed in an appropriate position between the patient's legs so that the body contact portion (14) of the flexible container (11) is just below the place where the urine exits from the user's body. When the portion (14) is pressed against the user's body, it will cause a seal to insure that all of the urine will pass into the flexible container (11). In addition, the top opening (13') of the flexible container is provided with an enlarged, oversized substantially circular configuration to allow the user to wipe herself subsequent to urination, but prior to withdrawl of the deformable lip portion (14') of the container (11) from contact with the user's vagina. As the urine is caught in the flexible container (11) it will immediately pass through the conduit (18), hose (17), conduit (20) and into the bottle (18). It will not flow through the opening (21) yet because the cap closure (22) will be in place during such use.

After the urine has been collected in the bottle (18), the cap (15) can be placed back on the flexible container (11) and the urinal can be stored by the user. With the cap (15) in place, everything which has had urine in contact with it will be covered, which is necessary when such devices are to be stored for any period of time. Later, when it is desired to empty the urinal, the flexible container (11), having the cap (15) still thereon and the bottle (18) is moved to the position shown in FIG. 8 so that the urine within the bottle (18) will flow down into the hose (17) but will not flow out through the top of container (11). Then the cap (22) is removed. After that, the open bottle (18) can be emptied into a toilet or other disposal place as shown in FIG. 9. Then it is convenient to cause water to flow from an adjacent sink into the container (11), for example in the position shown in FIG. 1, and allowing the rinsing water to flow through the container (18) and out through opening (21) into a toilet or the like. Disinfecting materials may be added to the water used to rinse the device if so desired.

Accordingly, it will be appreciated that the preferred embodiment does indeed accomplish the aforementioned objects. Obviously, many modifications and variations of the present invention are possible in light of the above teachings. It is therefore to be understood that, within the scope of the appended claims, the invention may be practised otherwise than as specifically described.

I claim:

1. A urinal for use by a female in a supine position consisting of:
    a plastic flexible container formed from a segment of a right circular cylinder, said container having a closed bottom and having a top rim portion formed by a plane passing through said right circular cylinder at an angle other than perpendicular to said right circular cylinder thus forming an uppermost and a lowermost segment of said rim portion;
    means disposed on said lowermost segment of said rim portion for contact with the body parts of a female person for causing urine flowing from such female person to flow into said container; wherein said means comprises a segment of said top rim portion comprising a special sealant section, comprising a short arcuate deformable lip portion formed on said lowermost segment of said rim portion of said flexible container wherein said special sealant section is a latex which is appreciably softer than the remainder of said top rim portion and has a modulus of elasticity substantially greater than the modulus of elasticity of said container for maintaining substantial contact between said special sealant section and a user's body when the remainder of said top rim portion is disposed in a generally horizontal disposition relative to the user's supine body leaving the said open top substantially unobstructed to permit wiping of the vaginal area of the user prior to the removal of the urinal from contact with the user's body;
    a first conduit means attached to a bottom portion of said flexible container in fluid communication with the bottom portion of said container;
    a bottle means for collecting and storing urine from said flexible container said bottle having an opening in the bottom thereof;
    a second conduit means attached in fluid communication with the top of said bottle means;
    flexible hose means attached in fluid communication, said first and second conduit means for causing urine in said flexible container to flow from said container to said bottle when said bottle is disposed below said container; and
    cap means for selectively slidably engaging said top rim of the container for selectively covering the top of said container.

* * * * *